(12) United States Patent
Pedersen et al.

(10) Patent No.: US 12,005,241 B2
(45) Date of Patent: *Jun. 11, 2024

(54) AUTO INJECTOR WITH DETECTION OF USED CARTRIDGE AND ASSOCIATED METHOD

(71) Applicant: Ascendis Pharma A/S, Hellerup (DK)

(72) Inventors: Per Mølgaard Pedersen, Struer (DK); Michael Lind, Ans (DK); Steen Jensen, Dragør (DK); Henrik Egesborg, Hellerup (DK)

(73) Assignee: Ascendis Pharma A/S, Hellerup (DK)

( * ) Notice: Subject to any disclaimer, the term of this patent is extended or adjusted under 35 U.S.C. 154(b) by 228 days.

This patent is subject to a terminal disclaimer.

(21) Appl. No.: 17/529,150

(22) Filed: Nov. 17, 2021

(65) Prior Publication Data

US 2022/0152310 A1 May 19, 2022

Related U.S. Application Data

(63) Continuation of application No. 16/060,593, filed as application No. PCT/EP2016/082860 on Dec. 29, 2016, now Pat. No. 11,179,524.

(30) Foreign Application Priority Data

Dec. 30, 2015 (EP) .................................... 15203172

(51) Int. Cl.
*A61M 5/315* (2006.01)
*A61M 5/20* (2006.01)
*A61M 5/24* (2006.01)

(52) U.S. Cl.
CPC ............ *A61M 5/3158* (2013.01); *A61M 5/20* (2013.01); *A61M 5/2422* (2013.01);
(Continued)

(58) Field of Classification Search
CPC ............ A61M 5/3158; A61M 5/31511; A61M 5/2422; A61M 5/20; A61M 2205/3368;
(Continued)

(56) References Cited

U.S. PATENT DOCUMENTS

| 4,024,864 A | 5/1977 | Davies |
| 4,677,980 A | 7/1987 | Reilly et al. |

(Continued)

FOREIGN PATENT DOCUMENTS

| CN | 101905048 | 12/2010 |
| CN | 102413855 | 4/2012 |

(Continued)

OTHER PUBLICATIONS

English translation of Office Action issued in Japanese Application No. 2019-570894, dated Jan. 13, 2022.

(Continued)

*Primary Examiner* — Lauren P Farrar
(74) *Attorney, Agent, or Firm* — Knobbe, Martens, Olson & Bear, LLP (57) ABSTRACT

Disclosed is an auto-injector for administering a medicament, comprising: a housing; a cartridge receiver configured to receive a cartridge comprising a first stopper; a drive module coupled to move a plunger rod configured to move the first stopper; a resistance sensor configured to provide a resistance signal indicative of resistance against movement of the plunger rod; and a processing unit coupled to the drive module and to the resistance sensor. The processing unit being configured to: control the drive module to move the plunger rod towards the extended plunger rod position; determine present plunger rod position; receive the resistance signal; determine a cartridge parameter based on the resistance signal and the present plunger rod position; and
(Continued)

control the drive module to adjust the movement of the plunger rod based on the cartridge parameter.

16 Claims, 7 Drawing Sheets

(52) U.S. Cl.
CPC . *A61M 5/31511* (2013.01); *A61M 2005/2086* (2013.01); *A61M 2005/2418* (2013.01); *A61M 2005/31588* (2013.01); *A61M 2205/276* (2013.01); *A61M 2205/3317* (2013.01); *A61M 2205/332* (2013.01); *A61M 2205/3327* (2013.01); *A61M 2205/3331* (2013.01); *A61M 2205/3365* (2013.01); *A61M 2205/3368* (2013.01); *A61M 2205/50* (2013.01); *A61M 2205/502* (2013.01); *A61M 2205/60* (2013.01); *A61M 2205/6063* (2013.01); *A61M 2205/82* (2013.01); *A61M 2205/8206* (2013.01)

(58) Field of Classification Search
CPC ...... A61M 2205/6063; A61M 2205/82; A61M 2205/60; A61M 2205/3365; A61M 2205/3331; A61M 2205/3327; A61M 2205/3317; A61M 2205/276; A61M 2005/2418; A61M 2005/2086; A61M 2205/8206; A61M 2205/502; A61M 2205/50; A61M 2205/332; A61M 2005/31588

See application file for complete search history.

(56) References Cited

U.S. PATENT DOCUMENTS

| | | |
|---|---|---|
| 5,739,508 A | 4/1998 | Uber, III |
| 5,808,203 A | 9/1998 | Nolan, Jr. et al. |
| 6,368,314 B1 | 4/2002 | Kipfer et al. |
| 9,173,995 B1 | 11/2015 | Tucker |
| 10,384,031 B1 | 8/2019 | Acker et al. |
| 10,835,677 B2 | 11/2020 | Fabricius et al. |
| 11,179,524 B2 | 11/2021 | Pedersen et al. |
| 11,351,305 B2 | 6/2022 | Pedersen et al. |
| 11,406,760 B2 | 8/2022 | Olesen et al. |
| 11,517,673 B2 | 12/2022 | Pedersen et al. |
| 11,524,115 B2 | 12/2022 | Jacobsen et al. |
| 11,607,496 B2 | 3/2023 | Fabricius et al. |
| 11,684,724 B2 | 6/2023 | Egesborg et al. |
| 11,738,147 B2 | 8/2023 | Olesen et al. |
| 2002/0016573 A1 | 2/2002 | Munk |
| 2002/0107477 A1 | 8/2002 | Kipfer |
| 2003/0083626 A1 | 5/2003 | Munk et al. |
| 2003/0205587 A1 | 11/2003 | Tribe |
| 2005/0261634 A1 | 11/2005 | Karlsson |
| 2006/0178630 A1 | 8/2006 | Bostrom et al. |
| 2009/0036846 A1 | 2/2009 | Dacquay et al. |
| 2009/0209883 A1 | 8/2009 | Higgins et al. |
| 2009/0299328 A1 | 12/2009 | Mudd et al. |
| 2010/0069842 A1 | 3/2010 | Dos Santos et al. |
| 2010/0094309 A1 | 4/2010 | Boukhny et al. |
| 2010/0211005 A1 | 8/2010 | Edwards et al. |
| 2011/0313395 A1 | 12/2011 | Krulevitch et al. |
| 2012/0078185 A1 | 3/2012 | Smith et al. |
| 2012/0204997 A1 | 8/2012 | Winn et al. |
| 2012/0283655 A1 | 11/2012 | Plumptre et al. |
| 2013/0079708 A1 | 3/2013 | Wiimpenny et al. |
| 2013/0193073 A1 | 8/2013 | Hogard et al. |
| 2013/0211326 A1 | 8/2013 | Dasbach et al. |
| 2013/0211327 A1 | 8/2013 | Osman et al. |
| 2013/0226134 A1 | 8/2013 | Schabbach et al. |
| 2013/0245545 A1 | 9/2013 | Arnold et al. |
| 2013/0281965 A1 | 10/2013 | Kamen et al. |
| 2013/0296807 A1 | 11/2013 | Lintern et al. |
| 2014/0012229 A1 | 1/2014 | Bokelman et al. |
| 2014/0114277 A1 | 4/2014 | Eggert et al. |
| 2014/0142514 A1 | 5/2014 | Elahi et al. |
| 2014/0166915 A1 | 6/2014 | Ishibashi et al. |
| 2014/0188076 A1 | 7/2014 | Kamen et al. |
| 2014/0193788 A1 | 7/2014 | Groves et al. |
| 2014/0207106 A1 | 7/2014 | Bechmann et al. |
| 2014/0221925 A1 | 8/2014 | Kondoh et al. |
| 2014/0358093 A1 | 12/2014 | Soerensen et al. |
| 2015/0045729 A1 | 2/2015 | Denzer et al. |
| 2015/0051538 A1 | 2/2015 | Hata et al. |
| 2015/0088089 A1 | 3/2015 | Bartlett, II et al. |
| 2015/0122338 A1 | 5/2015 | Hunter et al. |
| 2015/0231334 A1 | 8/2015 | Buchine et al. |
| 2015/0306316 A1* | 10/2015 | Bruggemann .......... A61M 5/20 604/67 |
| 2015/0320932 A1 | 11/2015 | Draper et al. |
| 2015/0359967 A1 | 12/2015 | Steel et al. |
| 2015/0367074 A1 | 12/2015 | Draper et al. |
| 2015/0367075 A1 | 12/2015 | Cave |
| 2015/0374930 A1 | 12/2015 | Hyde et al. |
| 2017/0119969 A1 | 5/2017 | McCullough et al. |
| 2017/0196702 A1 | 7/2017 | Agarwal |
| 2018/0094309 A1 | 4/2018 | Boukhany |
| 2018/0236181 A1 | 8/2018 | Marlin et al. |
| 2018/0369481 A1 | 12/2018 | Pedersen et al. |
| 2018/0369482 A1 | 12/2018 | Pedersen et al. |
| 2018/0369483 A1 | 12/2018 | Olesen et al. |
| 2019/0009028 A1 | 1/2019 | Jacobsen et al. |
| 2019/0009029 A1 | 1/2019 | Fabricius et al. |
| 2020/0384207 A1 | 12/2020 | Egesborg et al. |
| 2022/0288316 A1 | 9/2022 | Olesen et al. |
| 2023/0016657 A1 | 1/2023 | Pedersen et al. |
| 2023/0072178 A1 | 3/2023 | Jacobsen et al. |
| 2023/0090661 A1 | 3/2023 | Jensen et al. |
| 2023/0263961 A1 | 8/2023 | Egesborg et al. |
| 2023/0270945 A1 | 8/2023 | Fabricius et al. |
| 2023/0338659 A1 | 10/2023 | Olesen et al. |

FOREIGN PATENT DOCUMENTS

| | | |
|---|---|---|
| CN | 102740907 | 10/2012 |
| CN | 103813820 | 5/2014 |
| CN | 105492047 | 4/2016 |
| EP | 2656865 | 10/2013 |
| EP | 2675500 | 12/2013 |
| EP | 2777731 | 9/2014 |
| EP | 2923715 | 9/2015 |
| GB | 2356349 | 5/2001 |
| GB | 2506918 | 4/2014 |
| JP | H11513586 | 11/1999 |
| JP | 2000-513973 | 10/2000 |
| JP | 2005-503202 | 2/2005 |
| JP | 2005-080832 | 3/2005 |
| JP | 2008-531235 | 8/2008 |
| JP | 2009-279438 | 12/2009 |
| JP | 2010-506681 | 3/2010 |
| JP | 2010-510011 | 4/2010 |
| JP | 2010-523181 | 7/2010 |
| JP | 2011-507668 | 3/2011 |
| JP | 2011-521744 | 7/2011 |
| JP | 2011-240159 | 12/2011 |
| JP | 2012-505066 | 3/2012 |
| JP | 2012-066767 | 4/2012 |
| JP | 2012-516737 | 7/2012 |
| JP | 2012-519028 A | 8/2012 |
| JP | 2013-506444 | 2/2013 |
| JP | 2013-069305 | 4/2013 |
| JP | 2013-075154 | 4/2013 |
| JP | 2013-537844 | 10/2013 |
| JP | 2014-500746 | 1/2014 |
| JP | 2014-502890 | 2/2014 |
| JP | 2014-503279 | 2/2014 |
| JP | 2014-506159 | 3/2014 |
| JP | 2014-507223 | 3/2014 |
| JP | 2014-515941 | 7/2014 |
| JP | 2014-516700 | 7/2014 |
| JP | 2014-516702 | 7/2014 |
| JP | 2014-521113 | 8/2014 |

(56) References Cited

FOREIGN PATENT DOCUMENTS

| | | |
|---|---|---|
| JP | 2014-4528787 | 10/2014 |
| JP | 2015-521920 | 8/2015 |
| JP | 2015-163208 | 9/2015 |
| JP | 2016-208611 | 12/2016 |
| JP | 2001-513371 | 9/2021 |
| KR | 10-2015-0125701 | 11/2015 |
| KR | B-10-1666755 | 10/2016 |
| PT | 3397321 | 10/2022 |
| RU | 2014-120469 | 11/2015 |
| WO | WO 2002/051471 | 7/2002 |
| WO | WO 2005/102416 | 11/2005 |
| WO | WO 2006/116997 | 11/2006 |
| WO | WO 2008/062025 | 5/2008 |
| WO | WO 2006/059597 | 6/2008 |
| WO | WO 2010/098927 | 9/2010 |
| WO | WO 2010/098931 A1 | 9/2010 |
| WO | WO 2012/112347 | 8/2012 |
| WO | WO 2010/100883 | 9/2012 |
| WO | WO 2012/160157 | 11/2012 |
| WO | WO 2013/065055 | 5/2013 |
| WO | WO 2013/138830 | 9/2013 |
| WO | WO 2014/008393 | 1/2014 |
| WO | WO 2012/066767 | 5/2014 |
| WO | WO 2014/144096 | 9/2014 |
| WO | WO 2014/166915 | 10/2014 |
| WO | WO 2014/168205 | 10/2014 |
| WO | WO 2014/187812 | 11/2014 |
| WO | WO 2014/187813 | 11/2014 |
| WO | WO 2015/006430 | 1/2015 |
| WO | WO 2013/069305 | 4/2015 |
| WO | WO 2015/055640 | 4/2015 |
| WO | WO 2015/055642 | 4/2015 |
| WO | WO 2015/115326 | 8/2015 |
| WO | WO 2015/187797 | 12/2015 |
| WO | WO 2016/005421 | 1/2016 |
| WO | WO 2016/033507 | 3/2016 |
| WO | WO 2016/098060 | 6/2016 |
| WO | WO 2014/091765 | 1/2017 |
| WO | WO 2017/114906 | 7/2017 |
| WO | WO 2017/114907 | 7/2017 |
| WO | WO 2017/114908 | 7/2017 |
| WO | WO 2017/114909 | 7/2017 |
| WO | WO 2017/114910 | 7/2017 |
| WO | WO 2017/114911 | 7/2017 |
| WO | WO 2017/114912 | 7/2017 |
| WO | WO 2018/215516 | 11/2018 |
| WO | WO 2019/002534 | 1/2019 |
| WO | WO 2020/176319 | 9/2020 |
| WO | WO 2023/052487 | 4/2023 |

OTHER PUBLICATIONS

English translation of Office Action issued in Chinese Application No. 201880033657, dated Feb. 23, 2022.
English translation of Office Action issued in Japanese Application No. 2021-116315, dated Sep. 2, 2022.
English translation of Office Action issued in Korean Application No. 10-2020-7000564, dated Oct. 17, 2022.
Office Action in Canadian Application No. 3,006,626, dated Dec. 19, 2022, in 5 pages.
Office Action in Canadian Application No. 3,006,616, dated Dec. 19, 2022, in 3 pages.
Office Action in Canadian Application No. 3,006,638, dated Jan. 17, 2023, in 4 pages.
Office Action in Canadian Application No. 3,006,627, dated Dec. 30, 2022, in 5 pages.
Office Action in Canadian Application No. 3,006,643, dated Jan. 4, 2023, in 7 pages.
Office Action in Canadian Application No. 3,006,622, dated Jan. 4, 2023, in 4 pages.
English Translation of Office Action dated Jun. 3, 2021, in Corresponding Chinese Application No. 201880043795.0.
English Translation of Office Action dated Jul. 9, 2021, in corresponding Russian Application No. 2019140269.
English Translation of Office Action dated Jul. 30, 2021, in corresponding Russian Application No. 2020103216.
English Translation of Office Action dated Jun. 10, 2021, in corresponding Chinese Application No. 201880033657.4.
English translation of Office Action issued in Japanese Application No. 2019-565323, dated Jan. 5, 2022.
European Search Report for EP 15203132.4, dated Jun. 29, 2016.
European Search Report for EP 15203137.3, dated Jul. 1, 2016.
Partial European Search Report for EP15203168.8, dated Sep. 16, 2016.
International Search Report for PCT/EP2016/082861, dated Mar. 22, 2017.
International Preliminary Report on Patentability for PCT/EP2016/082861, dated Jul. 12, 2018.
International Search Report for PCT/EP2016/082856, dated Mar. 28, 2017.
International Preliminary Report on Patentability for PCT/EP2016/082856, dated Jul. 12, 2018.
International Search Report for PCT/EP2016/082860, dated May 3, 2017.
International Preliminary Report on Patentability for PCT/EP2016/082860, dated Jul. 12, 2018.
International Search Report for PCT/EP2016/082858, dated Mar. 24, 2017.
International Preliminary Report on Patentability for PCT/EP2016/082858, dated Jul. 12, 2018.
International Search Report for PCT/EP2016/082855, dated Mar. 24, 2017.
International Preliminary Report on Patentability for PCT/EP2016/082855, dated Jul. 12, 2018.
International Search Report for PCT/EP2016/082857, dated May 12, 2017.
International Preliminary Report on Patentability for PCT/EP2016/082857, dated Jul. 12, 2018.
International Search Report for PCT/EP2016/082859, dated Apr. 10, 2017.
International Preliminary Report on Patentability for PCT/EP2016/082859, dated Jul. 12, 2018.
International Search Report for PCT/EP2018/063460, dated Mar. 7, 2018.
International Preliminary Report on Patentability for PCT/EP2018/063460, dated Dec. 5, 2019.
International Search Report for PCT/EP2018/067532, dated Sep. 25, 2018.
International Preliminary Report on Patentability for PCT/EP2018/067532, dated Jan. 9, 2020.
European Search Report for EP 18733296.0, dated Feb. 1, 2023, in 5 pages.
Office Action in New Zealand Application No. 742523, dated Feb. 27, 2023, in 3 pages.
Office Action in New Zealand Application No. 742538, dated Mar. 8, 2023, in 9 pages.
Office Action in New Zealand Application No. 742526, dated Mar. 13, 2023, in 8 pages.
Office Action in Australian Application No. 2018-294519, dated Mar. 10, 2023, in 3 pages.
Hearing Notice dispatched on Dec. 29, 2023 in India Patent Application No. 201947041763.
English translation of Office Action issued in Japanese Application No. JP 2022-074131, dated Apr. 28, 2023, in 2 pages.
English translation of Office Action issued in Japanese Application No. JP 2021-116315, dated Apr. 25, 2023, in 3 pages.
Office Action in New Zealand Application No. 742526, dated Jul. 6, 2023, in 10 pages.
Office Action in Canadian Application No. 3,064,056, dated Jul. 11, 2023, in 5 pages.
English translation of Office Action issued in Japanese Application No. JP 2023-021789, dated Nov. 7, 2023, in 5 pages.

\* cited by examiner

AUTO INJECTOR WITH DETECTION OF USED CARTRIDGE AND ASSOCIATED METHOD

CROSS REFERENCE TO RELATED APPLICATIONS

This application is a continuation of U.S. application Ser. No. 16/060,593, filed Jun. 8, 2018, which is a U.S. National Phase Application of PCT International Application Number PCT/EP2016/082860, filed on Dec. 29, 2016, designating the United States of America and published in the English language, which is an International Application of and claims the benefit of priority to European Patent Application No. 15203172.0, filed on Dec. 30, 2015. The disclosures of the above-referenced applications are hereby expressly incorporated by reference in their entireties.

The present disclosure relates to an auto injector, such as an electronic auto injector, a system comprising an auto injector and a cartridge, and a method for operating an auto injector.

INTRODUCTION/BACKGROUND

Hypodermic syringes are widely used to deliver fluids to the body. It is known to have hypodermic syringes applicable for manual operation. However, auto injectors, such as electronic auto injectors, have been developed and are widely used to aid the administering of fluid or medicaments to the body.

To avoid relying on users correctly performing certain tasks, it is of increasing interest that the auto injector automatically carries out as much as possible of the injection process.

However, for safety of the user, it is of continuous desire that such auto injector prevents adverse use, securing or facilitating that the medicament is given appropriately, and that erroneous usage, or results of erroneous usage, e.g. incorrect dosage or transmission of infections, is prevented or reduced.

U.S. Pat. No. 5,808,203 discloses a pressure measuring device comprising a sensor to detect the force upon at least a portion of a contact surface of a syringe plunger during pressurization of a fluid medium within the syringe. Determination of the pressure of the fluid medium within the syringe is thereby enabled.

WO 2006/116997 discloses a handheld motor operated injection device comprising a motor for driving a piston rod operatively connected to a washer in order to inject a set dose of medicament from a cartridge containing the medicament. The injection device further comprises means for determining a reaction force generated in response to the motor driving the piston rod, the washer and a plunger in a forward axial direction in the cartridge.

US 2002/107477 discloses a device for administering an injectable product in doses. The device includes means for determining a malfunction of the device, and a vibrator motor is accommodated by the casing. The vibrator motor is triggered by the means for determining a malfunction such that it generates a vibrating alarm signal when a malfunction is determined.

SUMMARY

Despite the known solutions there is a need for an auto injector having an improved safety feature in order to prevent or reduce the risk of adverse use of the auto injector, or prevent or reduce the risks, such as health risks, resulting from adverse use of the auto injector. The present disclosure provides an auto injector, a system, and a method improving the safety of the auto injector and/or use of an auto injector.

Accordingly, an auto injector for administering a medicament is disclosed. The auto injector comprising: a housing, a cartridge receiver, a drive module, a resistance sensor and a processing unit.

The cartridge receiver is configured to receive a cartridge comprising a first stopper. The cartridge may comprise a medicament.

The drive module is coupled to move a plunger rod between a retracted plunger rod position and an extended plunger rod position. The plunger rod is configured to move the first stopper. The plunger rod may be configured to move the first stopper when the plunger rod is moved towards the extended plunger rod position.

The resistance sensor is configured to provide a resistance signal indicative of resistance against movement of the plunger rod.

The processing unit is coupled to the drive module and to the resistance sensor. The processing unit is configured to: control the drive module to move the plunger rod towards the extended plunger rod position, e.g. from the retracted plunger rod position; determine present plunger rod position; receive the resistance signal; and determine a cartridge parameter based on the resistance signal and the present plunger rod position. The processing unit may further be configured to control the drive module to adjust the movement of the plunger rod based on the cartridge parameter.

Also disclosed is a system comprising an auto injector, such as the disclosed auto injector, and a cartridge comprising a first stopper, wherein the cartridge is configured to be received in the cartridge receiver.

Also disclosed is a method for controlling an auto injector, such as the disclosed auto injector. The method comprising: receiving a cartridge comprising a first stopper, such as the cartridge of the disclosed system; moving a plunger rod, such as the plunger rod of the auto injector, towards an extended plunger rod position, e.g. towards the first stopper of the cartridge; determining present plunger rod position; receiving a resistance signal indicative of resistance against movement of the plunger rod; and determining a cartridge parameter based on the resistance signal and the present plunger rod position. The method may further comprise adjusting the movement of the plunger rod based on the cartridge parameter.

It is an advantage of the present disclosure that it may aid in determining characteristics of the received cartridge. It is a further advantage of the disclosure that an auto injector may be operated according to characteristics of the received cartridge.

For example, the disclosure provides a manner of determining or indicating that the cartridge received is a used cartridge and/or a flawed cartridge. Thus, an advantage of the disclosure may be that it increases the safety of an auto injector, e.g. as the auto injector may be prevented or restricted from using a not new cartridge.

Thus, it is a further advantage of the present disclosure, that patient safety is increased, e.g. by decreasing the risk of transmitting infections, and/or by decreasing the risk of incorrect dosage of medicament.

It is envisaged that any embodiments or elements as described in connection with any one aspect may be used with any other aspects or embodiments, mutatis mutandis.

Movement of the plunger rod may be adjusted based on the determined cartridge parameter. Adjusting the movement of the plunger rod may comprise stopping the movement of the plunger rod. Alternatively or additionally, adjusting the movement of the plunger rod may comprise moving the plunger rod to the retracted plunger rod position. For example, the cartridge parameter may be indicative of the cartridge being not full and/or empty. The movement of the plunger rod may be adjusted to stop and/or to move the plunger rod to the retracted position when the cartridge parameter is indicative of the cartridge being not full and/or empty.

The cartridge parameter may be indicative of the cartridge being not full and/or empty, such as used, e.g. if the present plunger rod position has reached a plunger rod threshold, such as a predetermined plunger rod position between the retracted plunger rod position and the extended plunger rod position, and the resistance signal being indicative of resistance against movement of the plunger rod below a low resistance threshold, e.g. indicating a small force necessary to move the plunger rod, hence indicating that the first stopper is in an advanced position. The low resistance threshold may be between 1 N and 15 N, such as between 5 N and 11 N. The low resistance threshold may be 1 N, 5 N, or 10 N.

Adjusting the movement of the plunger rod may comprise adjusting the movement of the plunger rod, such as stopping the movement of the plunger rod and/or moving the plunger rod to the retracted plunger rod position, if the cartridge parameter is indicative of the present plunger rod position having reached a plunger rod threshold and the resistance signal being indicative of resistance against movement of the plunger rod below a low resistance threshold. The processing unit may be configured to control the drive module to adjust movement of the plunger rod, such as stopping the movement of the plunger rod and/or moving the plunger rod to the retracted plunger rod position, if the cartridge parameter is indicative of the present plunger rod position having reached a plunger rod threshold and the resistance signal being indicative of resistance against movement of the plunger rod below a low resistance threshold.

The cartridge parameter may be indicative of the cartridge being flawed and/or that no needle is attached and/or attached needle is blocked, e.g. if the resistance signal is indicative of resistance against movement of the plunger rod above a high resistance threshold, e.g. indicating a large force necessary to move the plunger rod, hence indicating that the plunger rod and/or the first stopper is somehow blocked from advancement. The high resistance threshold may be between 8 N and 25 N, such as between 10 N and 20 N. The high resistance threshold may be 8 N, 11 N, or 15 N.

Adjusting the movement of the plunger rod may comprise adjusting the movement of the plunger rod, such as stopping the movement of the plunger rod and/or moving the plunger rod to the retracted plunger rod position, if the cartridge parameter is indicative of the resistance signal being indicative of resistance against movement of the plunger rod above a high resistance threshold. The processing unit may be configured to control the drive module to adjust movement of the plunger rod, such as stopping the movement of the plunger rod and/or moving the plunger rod to the retracted plunger rod position, if the cartridge parameter is indicative of the resistance signal being indicative of resistance against movement of the plunger rod above a high resistance threshold.

Thresholds, such as the plunger rod threshold, the low resistance threshold and/or the high resistance threshold, may be determined based on the cartridge and/or a cartridge code feature. The cartridge may comprise the cartridge code feature and/or the cartridge may form part of a cartridge assembly comprising the cartridge code feature. The cartridge code feature may be indicative of the threshold, such as the plunger rod threshold, the low resistance threshold and/or the high resistance threshold.

The auto injector may comprise a code sensor configured to read the cartridge code feature. The code sensor may provide a code signal indicative of the cartridge code feature. The processing unit may be coupled to the code sensor. The processing unit may be configured to receive the code signal. The processing unit may be configured to determine the threshold, such as the plunger rod threshold, the low resistance threshold and/or the high resistance threshold, based on the code signal.

The resistance signal may be provided by a resistance sensor. The resistance signal may be indicative of resistance against movement of the plunger rod, such as resistance against movement of the plunger rod in one direction, such as movement towards the extended plunger rod position, such as in a first plunger rod direction. For example, the resistance signal may be indicative of the force necessary to move the plunger rod, e.g. towards the extended plunger rod position.

The resistance against movement of the plunger rod may be determined by measuring and/or determining electrical power consumed by the drive module, e.g. by measuring electrical resistance, electrical current, and/or electrical voltage of the drive module.

The resistance sensor may be configured to determine electrical power consumed by the drive module, e.g. by measuring electrical resistance, electrical current, and/or electrical voltage of the drive module. The resistance sensor may comprise an electrical resistance sensor, an electrical current sensor, and/or an electrical voltage sensor. The resistance signal may be based on electrical power consumed by the drive module, such as on the determined electrical power consumed by the drive module. The drive module may comprise the resistance sensor.

The resistance sensor may be configured to measure pressure and/or force applied to a plunger rod front end of the plunger rod. The plunger rod front end may be configured to engage with the first stopper of the cartridge. The resistance sensor may be configured to measure pressure and/or force between the plunger rod and the stopper. For example, the resistance sensor may comprise a pressure transducer and/or a force transducer on the plunger rod front end. The plunger rod may comprise the resistance sensor.

The system may comprise a cartridge assembly. The cartridge may form part of a cartridge assembly, e.g. the cartridge assembly, such as the cartridge assembly of the system, may comprise the cartridge.

The cartridge receiver of the auto injector may be configured to receive the cartridge and/or cartridge assembly through a cartridge receiver opening. Thus, the cartridge and/or cartridge assembly may be inserted in the cartridge receiver through the cartridge receiver opening.

The cartridge may comprise a cartridge compartment. The cartridge compartment may be configured to contain a medicament. The cartridge compartment may contain a medicament.

The cartridge may comprise a cartridge outlet, e.g. at a first cartridge end. The cartridge outlet may be configured for fluid communication with the compartment, e.g. at the first cartridge end. The cartridge may be configured to expel medicament through the cartridge outlet. The cartridge outlet may be configured to be coupled with a needle, such as a hypodermic needle, to provide the medicament to be expelled through the needle. The cartridge assembly may comprise the needle and/or a needle assembly comprising the needle.

The cartridge may comprise a first stopper movable inside the cartridge compartment, e.g. towards the cartridge outlet, e.g. in a first stopper direction, such as towards the first cartridge end. For example, medicament may be expelled through the cartridge outlet upon movement of the first stopper, e.g. in the first stopper direction and/or towards the cartridge outlet.

The first stopper may be in an initial position, e.g. in an unused cartridge, such as a new cartridge. The first stopper may be in a final position, e.g. in a used cartridge, such as an empty cartridge. The first stopper may be in an advanced position between the initial position and the final position. The first stopper may be in an advanced position after having moved in the first stopper direction from the initial position.

The plunger rod of the auto injector is configured to move the first stopper. The first plunger rod direction may be the same as the first stopper direction when the cartridge is received in the cartridge receiver of the auto injector.

The cartridge may comprise a cartridge back face, e.g. at a second cartridge end, such as opposite the cartridge outlet. The cartridge back face may comprise a cartridge back end opening. The cartridge back end opening may provide access for the plunger rod to the first stopper.

The auto injector may be an electronic auto injector. The auto injector may comprise a battery. The housing may accommodate the battery. The battery may be a rechargeable battery. For example, the battery may be a Li-ion battery or a NiCd battery or a NiMH battery. The battery may be configured to be charged by connection of a charger.

The drive module is coupled to move, such as actuate, such as advance, the plunger rod. The drive module may comprise one or more electrical elements. The drive module may be configured to receive electrical power from the battery. The drive module may be electrically connected to the battery for receiving electrical power. The drive module may be accommodated by the housing. The drive module may comprise a motor, such as an electro-mechanical motor, such as a DC motor, e.g. a DC motor with or without brushes. The drive module may comprise a solenoid motor. The drive module may comprise a shape memory metal engine. The drive module may comprise an arrangement of springs configured to actuate the plunger rod. The drive module may comprise a pressurized gas configured to actuate the plunger rod.

The plunger rod may be configured to move, such as advance a first stopper, such as the first stopper of the cartridge. The movement of the first stopper may be to expel medicament from the cartridge compartment through the cartridge outlet and/or to expel air from the cartridge compartment through the cartridge outlet.

The plunger rod position, such as the present plunger rod position, such as the plunger rod position at a specific moment in time, may be determined, e.g. by the processing unit. The present plunger rod position may be determined based on detection from a sensor, such as an ejection sensor and/or a tachometer.

The auto injector may comprise an ejection sensor, e.g. configured to detect the ejection, such as the expelling, of medicament and/or air in the cartridge compartment. The ejection sensor may be configured to detect the position of the plunger rod and/or the position of the first stopper.

The auto injector may comprise a tachometer, e.g. a tachometer of the drive module. The ejection sensor may comprise the tachometer. The tachometer may be configured to count the revolutions of the drive module, such as a motor of the drive module, such as the revolutions of the drive module from a set point, such as a point wherein the position of the plunger rod is known, such as the retracted plunger rod position, such as a fully retracted position of the plunger rod. The count of revolutions of the drive module may be used to determine the present plunger rod position, i.e. the position of the plunger rod at a specific moment in time.

The tachometer may be configured to provide a tachometer signal indicative of a count of revolutions of the drive module. The processing unit may be coupled to the tachometer. The processing unit may be configured to receive the tachometer signal. The processing unit may be configured to determine the present plunger rod position based on the tachometer signal.

The processing unit may be coupled to the ejection sensor. The processing unit may receive from the ejection sensor a first ejection sensor signal, such as the tachometer signal, indicative of the count of revolutions of the drive module. The processing unit may determine the position of the plunger rod based on the first ejection sensor signal, e.g. the tachometer signal. The processing unit may receive a second ejection sensor signal, e.g. from the ejection sensor, indicative of the plunger rod being in a known position, such as in the retracted plunger rod position, such as a fully retracted position. The processing unit may be configured to determine the position of the plunger rod based on the first ejection sensor signal, e.g. the tachometer signal, and the second ejection sensor signal. The processing unit may be configured to determine the present plunger rod position based on the tachometer signal and the retracted plunger rod position. For example, the processing unit may be configured to determine the present plunger rod position based on the number of revolutions of the drive module since the plunger rod was in the retracted plunger rod position.

The auto injector may comprise a user interface, such as a user interface allowing user input and/or provide a user output signal, such as a visual output signal and/or an audible output signal to the user.

The user interface may comprise one or more input members including a first input member and/or a second input member. The first input member and/or the second input member may comprise a button.

The user interface may comprise one or more output members including a first output member and/or a second output member. The first output member and/or the second output member may comprise a loudspeaker and/or a visual display and/or an LED and/or a plurality of LEDs.

The user interface may be coupled to the processing unit. The processing unit may be configured to output a user output signal via the user interface, e.g. based on the cartridge parameter. The user output signal may be based on the cartridge parameter. For example, the user output signal may be indicative of the cartridge parameter. Thus, for example, the auto injector may be configured to signal to the user that the received cartridge cannot be used and/or the auto injector may be configured to signal to the user why the received cartridge cannot be used.

BRIEF DESCRIPTION OF THE FIGURES

A more detailed description follows below with reference to the drawing, in which.

DETAILED DESCRIPTION

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment need not have all the aspects or advantages shown. An aspect or an advantage described in conjunction with a particular embodiment is not necessarily limited to that embodiment and can be practiced in any other embodiments even if not so illustrated, or if not so explicitly described.

Figure 1:
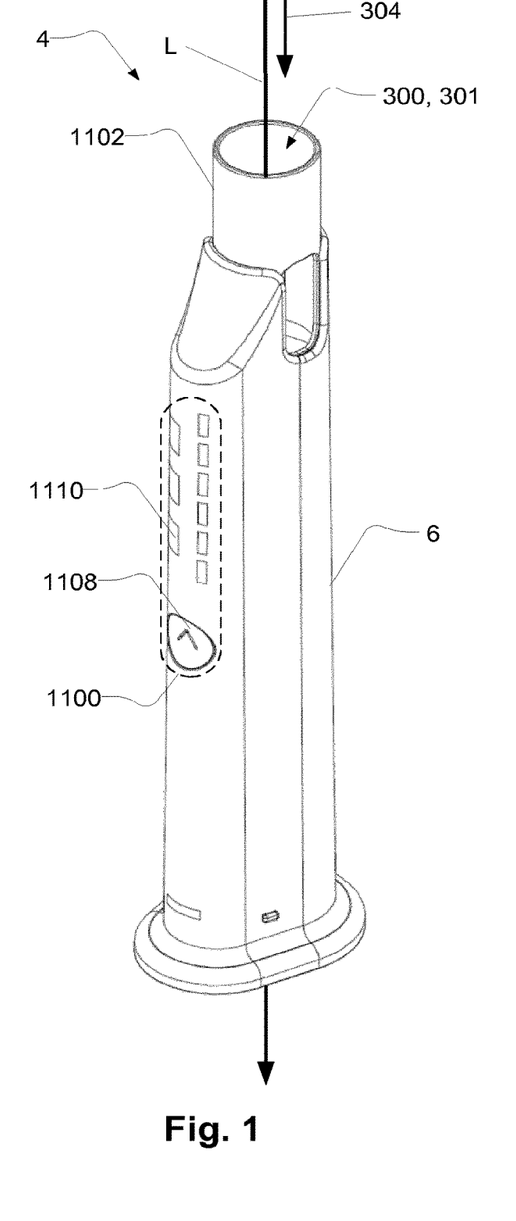
FIG. 1 illustrates an exemplary auto injector.

FIG. 1 illustrates an exemplary auto injector 4. The auto injector 4 may be configured for administering a medicament. The auto injector 4 may be an electronic auto injector.

The auto injector 4 comprises a housing 6. The auto injector 4 comprises a cartridge receiver 300. The cartridge receiver is configured to receive a cartridge and/or a cartridge assembly comprising a cartridge. The cartridge may contain the medicament.

The cartridge receiver 300 has a cartridge receiver opening 301. The cartridge receiver 300 is configured to receive the cartridge and/or the cartridge assembly through the cartridge receiver opening 301 in a cartridge receiving direction 304 along a longitudinal axis L.

The auto injector 4 may comprise a user interface 1100, as illustrated. The auto injector 4 comprises a trigger member, such as the contact member 1102. The contact member 1102 may be configured to be pressed against an injection site. The contact member 1102 may be movable in the cartridge receiving direction 304, relative to the housing, if pressed against the injection site. The contact member 1102 may be part of the user interface 1100.

The user interface 1100 may comprise a first input member 1108 as illustrated, e.g. a button. The first input member 1108 may provide for a user input from a user. For example, the first input member 1108 may be used for receiving a push from a user to proceed to a next step.

The user interface 1100 may comprise a first output member 1110 as illustrated, e.g. a plurality of LEDs. The first output member 1110 may provide for a user output to a user. The user interface 1100 may comprise a second output member (not shown), e.g. a speaker. The second output member may be configured to provide audible output to the user. For example, the first output member 1110 and/or the second output member may be used to indicate a step in the procedure to the user and/or to indicate an error message.

Figure 2:
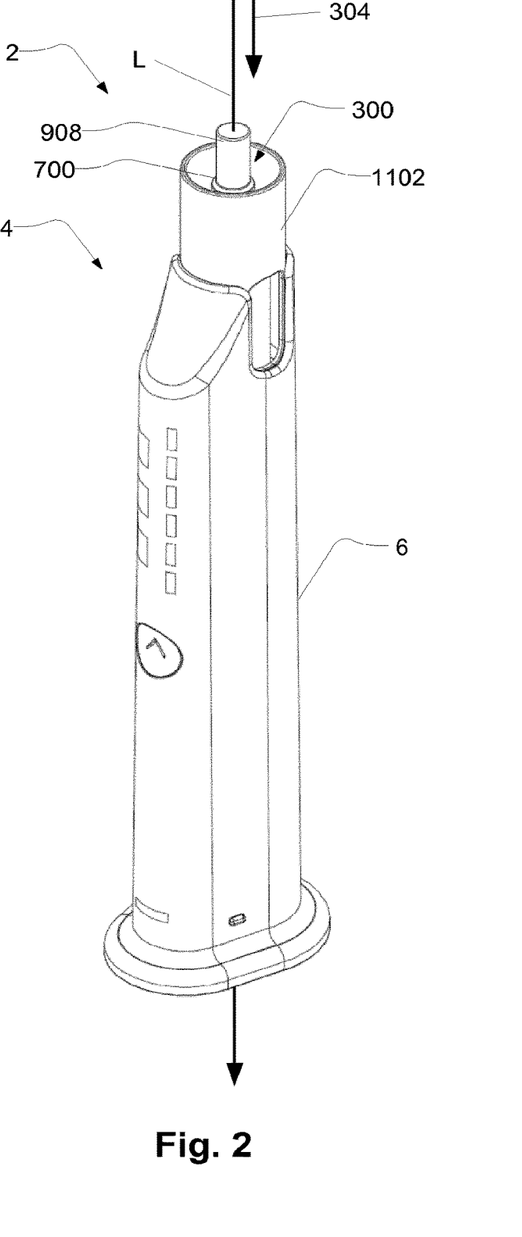
FIG. 2 illustrates an exemplary auto injector with a cartridge.

FIG. 2 illustrates an exemplary system 2. The system 2 comprises an auto injector 4, as described in relation to FIG. 1, and an exemplary cartridge 700 received in the cartridge receiver 300. The cartridge 700 is shown with a needle cover 908. The needle cover 908 extending out of the contact member 1102 to allow removal of the needle cover 908 from the cartridge 700.

Figure 3:
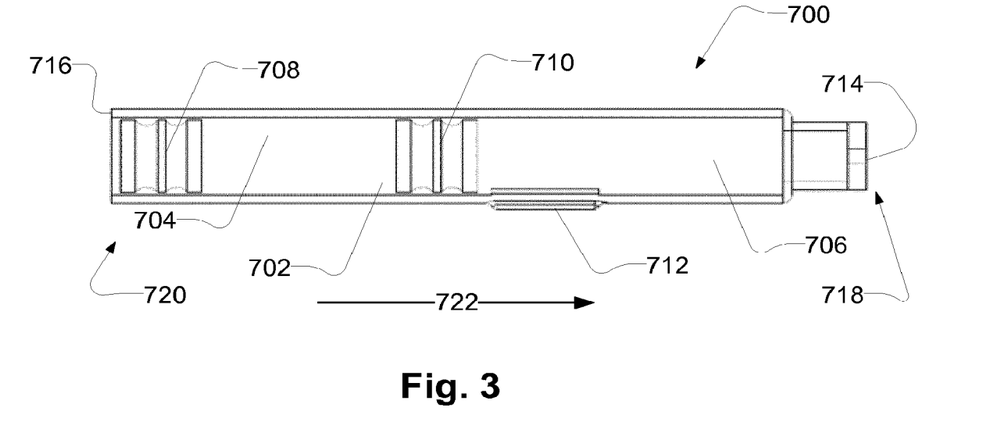
FIG. 3 schematically illustrates an exemplary cartridge.

FIG. 3 schematically illustrates an exemplary cartridge 700, such as a cartridge 700 being configured to be received in the cartridge receiver of an auto injector, such as the auto injector described in relation to previous figures.

The cartridge 700 comprises a cartridge compartment 702. The cartridge compartment 702 may be configured for containing a medicament. The cartridge 700 has a first end 718 and a second end 720. The cartridge 700 comprises a cartridge outlet 714 at the first cartridge end 718. The cartridge may be configured to expel medicament through the cartridge outlet 714.

The cartridge comprises a first stopper 708 movable inside the cartridge compartment 702, e.g. in a first stopper direction 722, e.g. towards the first cartridge end 718. For example, the medicament may be expelled through the cartridge outlet 714 upon movement of the first stopper 708 in the first stopper direction 722. The cartridge 700 comprises a cartridge back face 716 at the second cartridge end 720. The cartridge back face 716 comprises a cartridge back end opening for providing access to the first stopper 708 for a plunger rod.

As illustrated, the cartridge 700 may be a dual chamber cartridge. The cartridge comprises a second stopper 710 movable inside the cartridge compartment 702, e.g. in the first stopper direction 722, e.g. towards the first cartridge end 718. The cartridge compartment 702 comprises a first cartridge subcompartment 704 and a second cartridge subcompartment 706. The first cartridge subcompartment 704 is between the first stopper 708 and the second stopper 710. The first cartridge subcompartment 704 may comprise a liquid, such as sterile water or a buffer solution. The second cartridge subcompartment 706 is between the second stopper 710 and the cartridge outlet 714. The second cartridge subcompartment 706 may comprise a medicament, such as a dry medicament, such as a medicament dried by lyophilization. The cartridge comprises a bypass section 712 for providing fluid communication between the first cartridge subcompartment 704 and the second cartridge subcompartment 706. The bypass section 712 provides fluid communication between the first cartridge subcompartment 704 and the second cartridge subcompartment 706 when the second stopper 710 is positioned in the bypass section 712.

Figure 4:
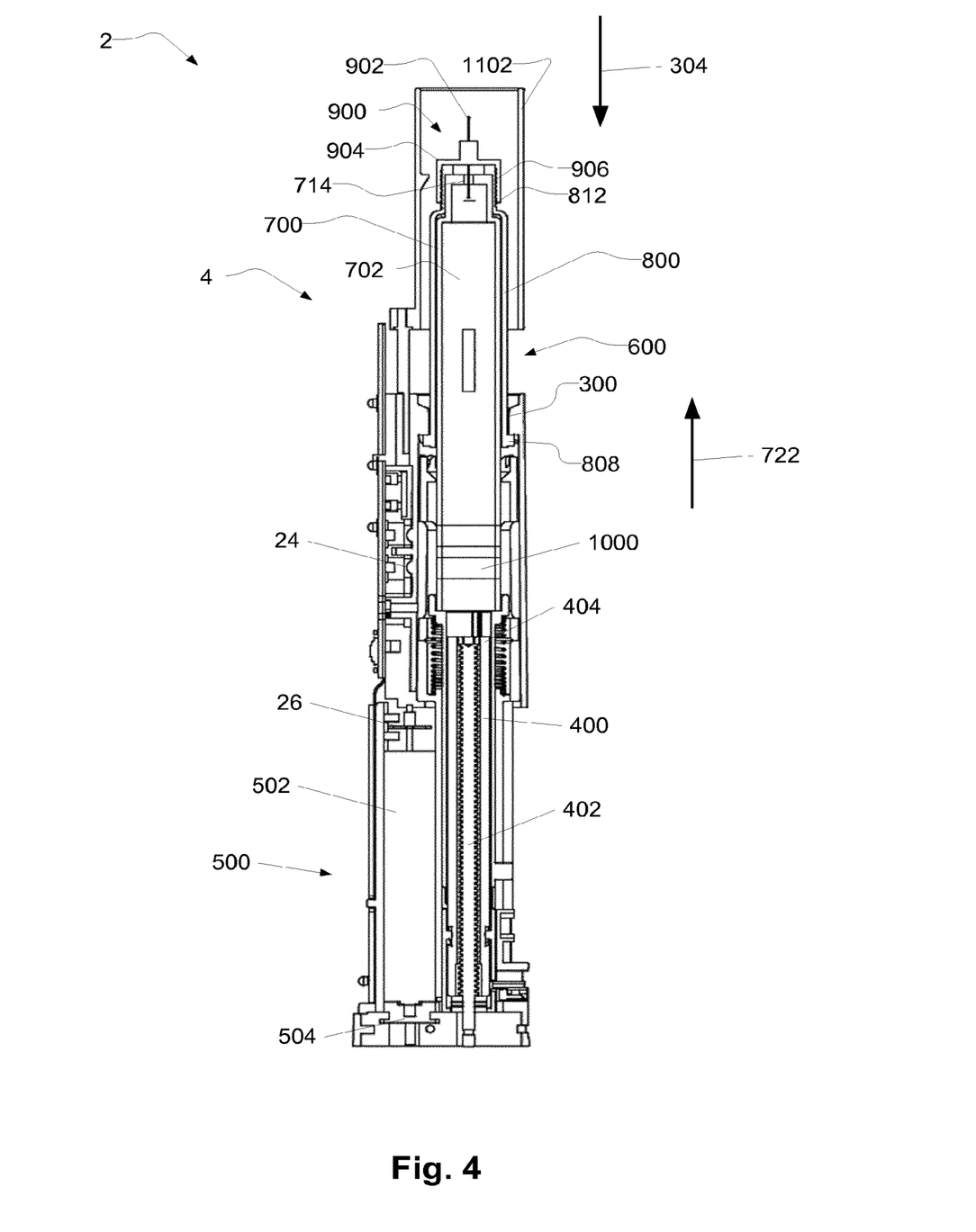
FIG. 4 schematically illustrates an exemplary auto injector with a cartridge.

FIG. 4 illustrates an exemplary system 2. The system 2 comprises an auto injector 4, as described, for example, in relation to FIG. 1, and an exemplary cartridge assembly 600. The cartridge assembly 600 comprises a cartridge 700 with a cartridge compartment 702, a needle assembly 900, and an optional cartridge code feature 1000. The cartridge assembly 600 is received in the auto injector 4.

The cartridge assembly 600 comprises a cartridge holder 800. The cartridge holder is configured for retention of the cartridge 700 in the cartridge receiver 300 of the auto injector 4. The cartridge holder 800 comprises a cartridge retention member 808. The cartridge retention member engages with the cartridge receiver 300 for reception of the cartridge 700 and the cartridge assembly 600 in the cartridge receiver.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700. The cartridge outlet 714 may be blocked by a resilient sealing being penetrated by the needle 902, when the needle assembly 900 is attached to the cartridge 700.

The auto injector 4 comprises an optional code sensor 24 configured to read the cartridge code feature 1000. When the cartridge assembly 600 is inserted, as shown, the cartridge code feature 1000 is lined up with the code sensor 24.

The auto injector 4 comprises a plunger rod 400. The plunger rod 400 is configured to advance a first stopper of the cartridge 700. The plunger rod 400 comprises an outer plunger rod 404 with an inner thread, and an inner plunger rod 402 with an outer thread. The thread of the inner plunger rod 402 is in engagement with the thread of the outer plunger rod 404. The outer plunger rod 404 is prevented from rotating relative to the housing of the auto injector. The movement of the plunger rod 400 comprises rotation of the inner plunger rod 402. The rotation of the inner plunger rod 402 results in translational movement of the outer plunger rod 404, due to the outer plunger rod 404 being rotationally restricted. The outer plunger rod 404, when moved translationally in the first stopper direction 722, is configured to abut the first stopper of the cartridge 700, and to move the first stopper in the first stopper direction 722.

The drive module 500 is coupled to actuate the plunger rod 400. The drive module 500 is electrically connected to a battery for receiving electrical power. The drive module 500 comprises a motor 502, such as an electro-mechanical motor, such as a DC motor. The drive module 500 comprises a transmission 504 for coupling the motor 502 to the inner plunger rod 402 of the plunger rod 400.

Although the example shown comprises a motor 502, which may be an electro-mechanical motor, it will be readily understood that the auto injector 4 may be realised having an alternative drive module, such as comprising a solenoid motor, a shape memory metal engine, an arrangement of springs and/or a pressurized gas configured to actuate the plunger rod 400.

The auto injector 4 comprises an ejection sensor 26, such as a plunger rod position sensor. The ejection sensor 26 is configured to detect the position of the plunger rod 400. In the illustrated example, the ejection sensor 26 comprises a tachometer configured to count/detect the revolutions of the motor 502. Thus, the position of the plunger rod 400 may be determined. The ejection sensor 26 may, based on the detection of the position of the plunger rod 400, detect the expelling of medicament and/or air in the cartridge compartment. The position of the plunger rod 400 is indicative of the position of the first stopper 708 of the cartridge 700.

Figure 5:
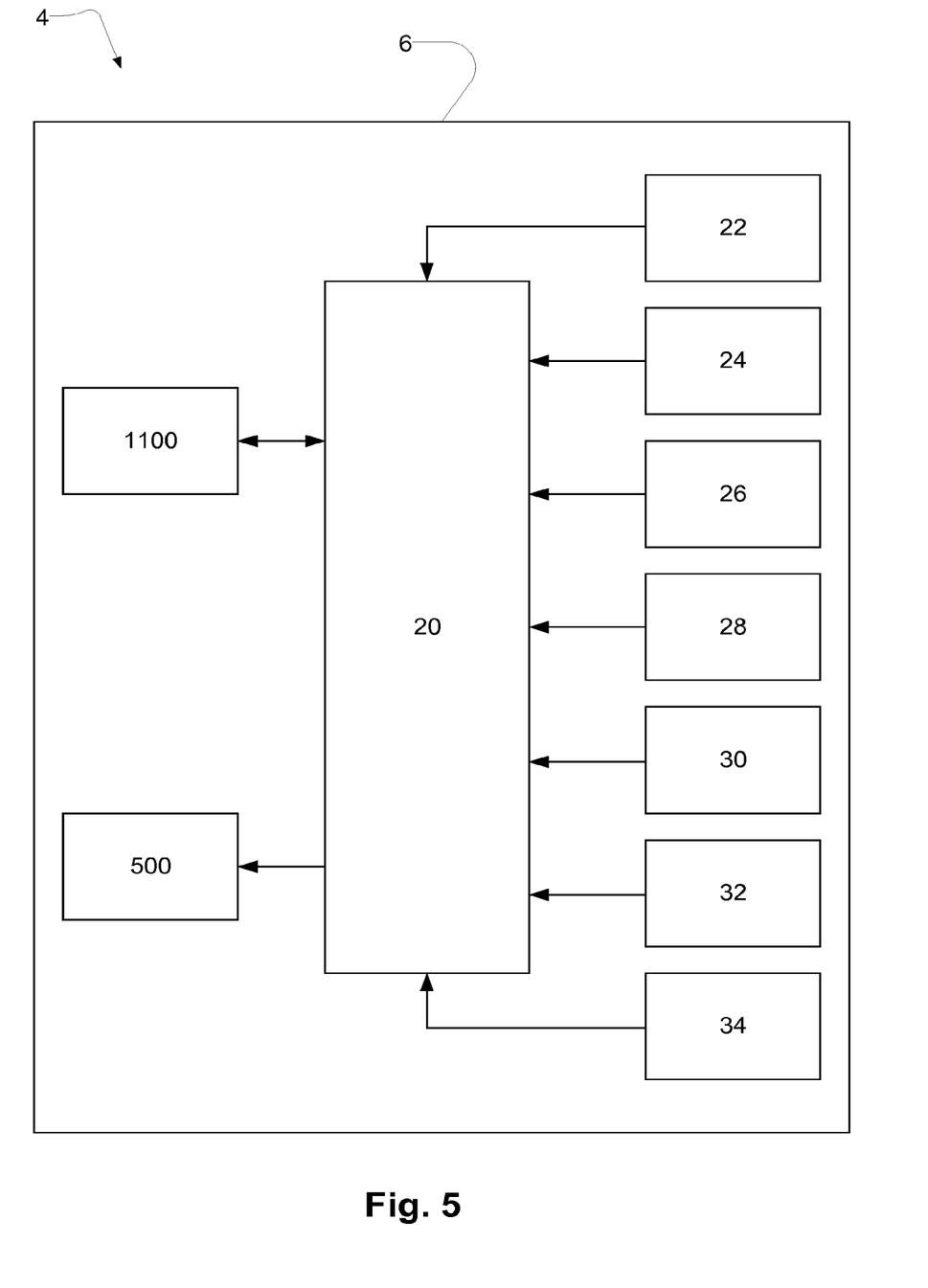
FIG. 5 shows a block diagram of an exemplary auto injector.

FIG. 5 shows a block diagram of an exemplary auto injector 4. The auto injector 4 comprises a plurality of sensors 22, 24, 26, 28, 30, 32, 34, a processing unit 20, a drive module 500, and a user interface 1100. The sensors 22, 24, 26, 28, 30, 32, 34 are coupled to the processing unit 20. The user interface 1100 is coupled to the processing unit 20. The processing unit is coupled to the drive module 500.

The processing unit 20 receives signals from the sensors 22, 24, 26, 28, 30, 32, 34 and the user interface 1100. The processing unit 20 is configured to control the drive module 500. The processing unit 20 may control the drive module 500 based on one or more of the received signals from the sensors 22, 24, 26, 28, 30, 32, 34 and the user interface 1100.

The auto injector 4 comprises an orientation sensor 22. The orientation sensor 22 is configured to provide an orientation signal indicative of the orientation of a cartridge received in the auto injector 4. For example, the orientation sensor 22 may be configured to detect the orientation of the auto injector 4. The orientation of the cartridge may be determined based on the orientation of the auto injector 4. The orientation sensor 22 may be configured to detect the direction of gravity. For example, the orientation sensor 22 may comprise an accelerometer.

The processing unit 20 is coupled to the orientation sensor 22. The processing unit 20 is configured to receive the orientation signal. The processing unit 20 may determine the orientation of the cartridge based on the orientation signal. The processing unit 20 may control the drive module 500 based on the orientation signal. For example, the processing unit 20 may be configured to control the drive module 500 to move the plunger rod based on the orientation signal. For example, the processing unit 20 may be configured to control the drive module 500 to move the plunger rod towards an extended plunger rod position only if the cartridge outlet is pointing upwards. Alternatively or additionally, the processing unit 20 may provide user output via the user interface 1100 based on the orientation signal.

The auto injector 4 comprises a code sensor 24. The code sensor 24 is configured to read a cartridge code feature, and provide a code signal indicative of a cartridge code feature. For example, the code sensor may be configured to read/detect a colour code.

The processing unit 20 is coupled to the code sensor 24. The processing unit 20 is configured to receive the code signal. The processing unit 20 may determine the cartridge code feature of the cartridge assembly based on the code signal. The processing unit 20 may be configured to determine a threshold, such as a plunger rod threshold, based on the code signal. The processing unit 20 may control the drive module 500 based on the code signal. For example, the processing unit 20 may be configured to control the drive module 500 to move the plunger rod towards the extended plunger rod position based on the code signal. Alternatively or additionally, the processing unit 20 may provide user output via the user interface 1100 based on the code signal.

The auto injector 4 comprises an ejection sensor 26, such as a plunger rod position sensor. The ejection sensor 26 is configured to detect the position of the plunger rod of the auto injector 4, and provide an ejection sensor signal indicative of the position of the plunger rod. The ejection sensor 26 may comprise a tachometer coupled to the drive module 500.

The processing unit 20 is coupled to the ejection sensor 26. The processing unit 20 is configured to receive the ejection sensor signal. The processing unit 20 may determine the position of the plunger rod based on the ejection sensor signal. The processing unit 20 may control the drive module 500 based on the ejection sensor signal. For example, the processing unit 20 may be configured to control the drive module 500 to start, stop or continue movement of the plunger rod based on the ejection sensor signal. For example, the processing unit 20 may be configured to determine a present plunger rod position based on the ejection sensor signal. Alternatively or additionally, the processing unit 20 may provide user output via the user interface 1100 based on the ejection sensor signal.

The auto injector 4 comprises a cartridge sensor 28. The cartridge sensor 28 is configured to detect reception of a cartridge assembly in the auto injector 4. The cartridge sensor 28 provides a cartridge sensor signal indicative of reception of a cartridge assembly.

The processing unit 20 is coupled to the cartridge sensor 28. The processing unit 20 is configured to receive the cartridge sensor signal. The processing unit 20 may control the drive module 500 based on the cartridge sensor signal. For example, the processing unit 20 may be configured to control the drive module 500 to start movement of the plunger rod if a cartridge assembly is received, and/or only if a cartridge assembly is received. Alternatively or additionally, the processing unit 20 may provide user output via the user interface 1100 based on the cartridge sensor signal.

The code sensor 24 and the cartridge sensor 28 may be the same sensor, e.g. the code sensor 24 may be configured to detect reception of a cartridge assembly and subsequently read the cartridge code feature.

The auto injector 4 comprises a needle sensor 30. The needle sensor 30 is configured to detect a needle, and/or a needle assembly, and/or a needle cover of a needle assembly, of the cartridge assembly, when the cartridge assembly is received in the auto injector 4. The needle sensor 30 provides a needle signal indicative of the presence of a needle, and/or a needle assembly, and/or a needle cover of a needle assembly, of the cartridge assembly.

The processing unit 20 is coupled to the needle sensor 30. The processing unit 20 is configured to receive the needle signal. The processing unit 20 may control the drive module 500 based on the needle signal. For example, the processing unit 20 may be configured to control the drive module 500 to start movement of the plunger rod only if a needle is present, and/or only if a needle cover is not present, such as removed. Detection of a needle cover may be indicative of a needle being present. The processing unit 20 may be configured to control the drive module 500 to start only if a needle cover has been detected, and afterwards removed. Alternatively or additionally, the processing unit 20 may provide user output via the user interface 1100 based on the needle signal.

The auto injector 4 comprises a temperature sensor 32. The temperature sensor 32 is configured to detect a temperature, such as a temperature of the auto injector and/or of the cartridge and/or of the medicament. The temperature sensor 32 is configured to provide a temperature signal indicative of the temperature.

The processing unit 20 is coupled to the temperature sensor 32. The processing unit 20 is configured to receive the temperature signal. The processing unit 20 may be configured to determine the temperature, such as the temperature of the auto injector and/or of the cartridge and/or of the medicament based on the temperature signal. The processing unit 20 may control the drive module 500 based on the temperature signal. For example, the processing unit 20 may be configured to control the drive module 500 to move the plunger rod towards the extended plunger rod position based on the temperature signal. Alternatively or additionally, the processing unit 20 may provide user output via the user interface 1100 based on the temperature signal.

The auto injector 4 comprises a resistance sensor 34. The resistance sensor 34 is configured to detect resistance against movement of the plunger rod of the auto injector 4. The resistance sensor 34 may be configured to detect resistance against movement of the plunger rod based on measurements of the drive module 500. For example, the resistance sensor 34 may be configured to detect the electrical current of a motor of the drive module 500. The resistance sensor 34 is configured to provide a resistance signal indicative of resistance against movement of the plunger rod.

The processing unit 20 is coupled to the resistance sensor 34. The processing unit 20 is configured to receive the resistance signal. The processing unit 20 may be configured to determine the resistance against movement of the plunger rod based on the resistance signal. The processing unit 20 may control the drive module 500 based on the resistance signal. For example, the processing unit 20 may be configured to control the drive module 500 to adjust movement of the plunger rod based on the resistance signal. For example, the processing unit 20 may be configured to control the drive module 500 to start, stop or continue movement of the plunger rod based on the resistance signal. Alternatively or additionally, the processing unit 20 may provide user output via the user interface 1100 based on the resistance signal.

The auto injector 4 is illustrated comprising all of the above mentioned sensors. However, alternatively, the auto injector may comprise only one or any combination of one or more of the above mentioned sensors.

The auto injector comprises a user interface 1100. The user interface 1100 may comprise one or more input members, e.g. a first input member, for receiving a user input. The user interface is configured to provide a user input signal indicative of the received user input.

The processing unit 20 is coupled to the user interface 1100. The processing unit 20 is configured to receive the user input signal. The processing unit 20 may control the drive module 500 based on the user input signal. For example, the processing unit 20 may be configured to control the drive module 500 to move the plunger rod towards the extended plunger rod position based on the user input signal.

The auto injector comprises a housing 6 accommodating the sensors 22, 24, 26, 28, 30, 32, 34, processing unit 20, user interface 1100 and drive module 500.

Figure 6:
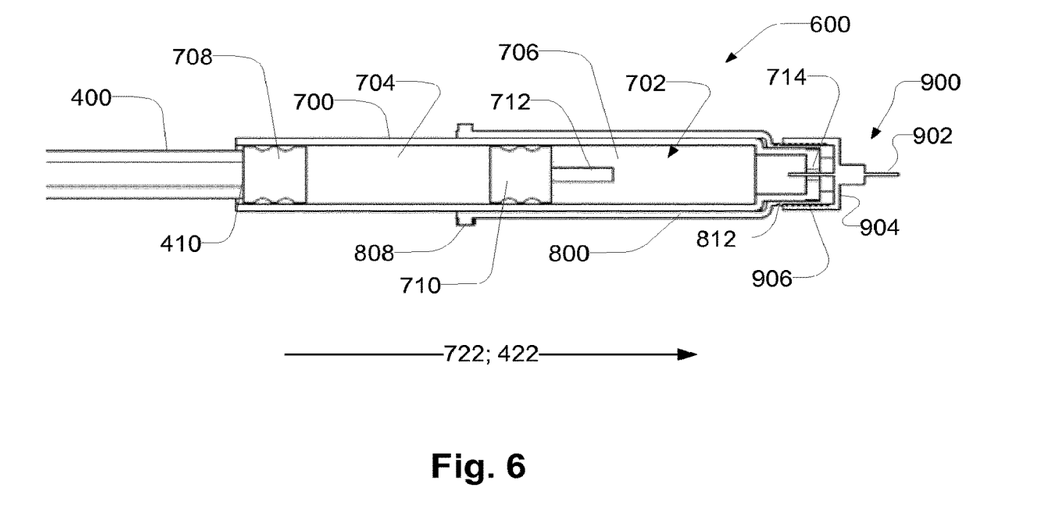
FIG. 6 schematically illustrates an exemplary cartridge and a plunger rod.
Figure 7:
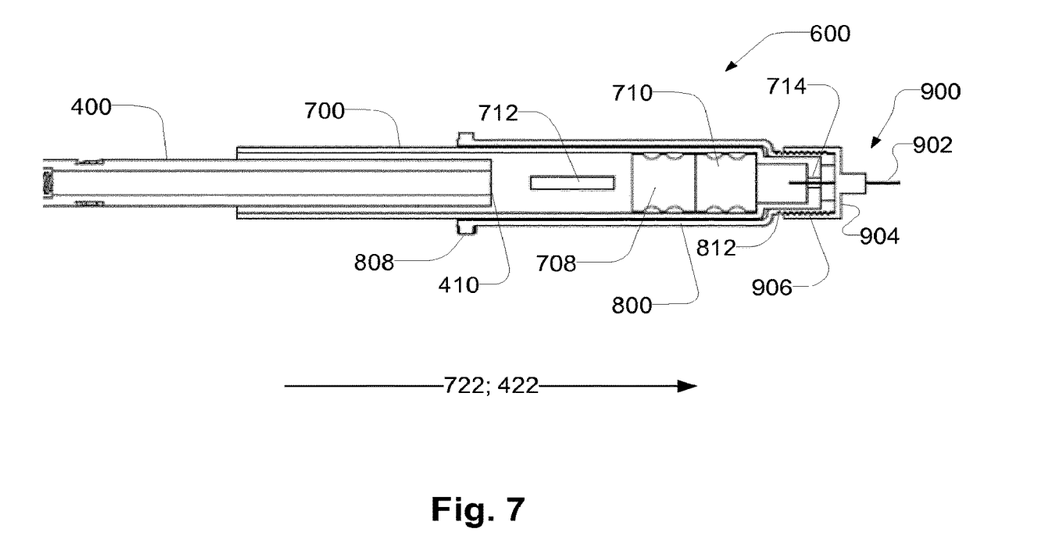
FIG. 7 schematically illustrates an exemplary cartridge and a plunger rod.

FIG. 6 and FIG. 7 schematically illustrate exemplary cartridge assemblies 600 and a plunger rod 400. The cartridge assembly 600 comprises a cartridge 700, such as the cartridge described in relation to FIG. 3, a cartridge holder 800, and a needle assembly 900. For intelligibility, the auto injector comprising the plunger rod 400 is not shown.

The cartridge holder 800 comprises a cartridge retention member 808. The cartridge retention member 808 is configured for engagement with a cartridge receiver of the auto injector. The cartridge holder 800 comprises a needle assembly coupling portion 812. The needle assembly coupling portion 812 is configured for engagement with a cartridge holder coupling portion 906 of the needle assembly 900. The needle assembly coupling portion 812 allows attachment of a needle to the cartridge 700.

The needle assembly 900 comprises a needle 902 and a needle hub 904. The needle assembly 900 is attached to the cartridge 700, e.g. by the needle hub 904 having a cartridge holder coupling portion 906, e.g. a threaded coupling portion, being in engagement with a needle assembly coupling portion 812 of the cartridge holder 800. The needle 902 extends through the cartridge outlet 714 of the cartridge 700.

FIG. 6 schematically illustrates a situation wherein an unused cartridge, such as a new cartridge, is received. The first stopper 708 is positioned in initial position. The plunger rod 400 has moved towards the extended plunger rod position, such that in the present plunger rod position a plunger rod front end 410 of the plunger rod 400 abuts the first stopper 708. Thus, further movement of the plunger rod 400 towards the extended plunger rod position, e.g. in the first plunger rod direction 422, will lead to the first stopper 708 to be moved, e.g. in the first stopper direction 722. Movement of the plunger rod 400 towards the extended plunger rod position will require an increased force after abutment of the plunger rod front end 410 to the first stopper 708, e.g. due to frictional force between the first stopper 708 and inner walls of the cartridge compartment 702.

FIG. 7 schematically illustrates a situation wherein a used cartridge, such as an empty cartridge, is received. The first stopper 708 is positioned in a final position, such as an advanced position, e.g. advanced in the first stopper direction 722 compared to an initial position. The plunger rod 400 has moved towards the extended plunger rod position, such that in the present plunger rod position the plunger rod 400 extends into the cartridge 700. Compared to the situation described in FIG. 6, movement of the plunger rod 400 towards the extended plunger rod position does not require an increased force since the plunger rod front end 410 does not abut the first stopper 708.

Figure 8:
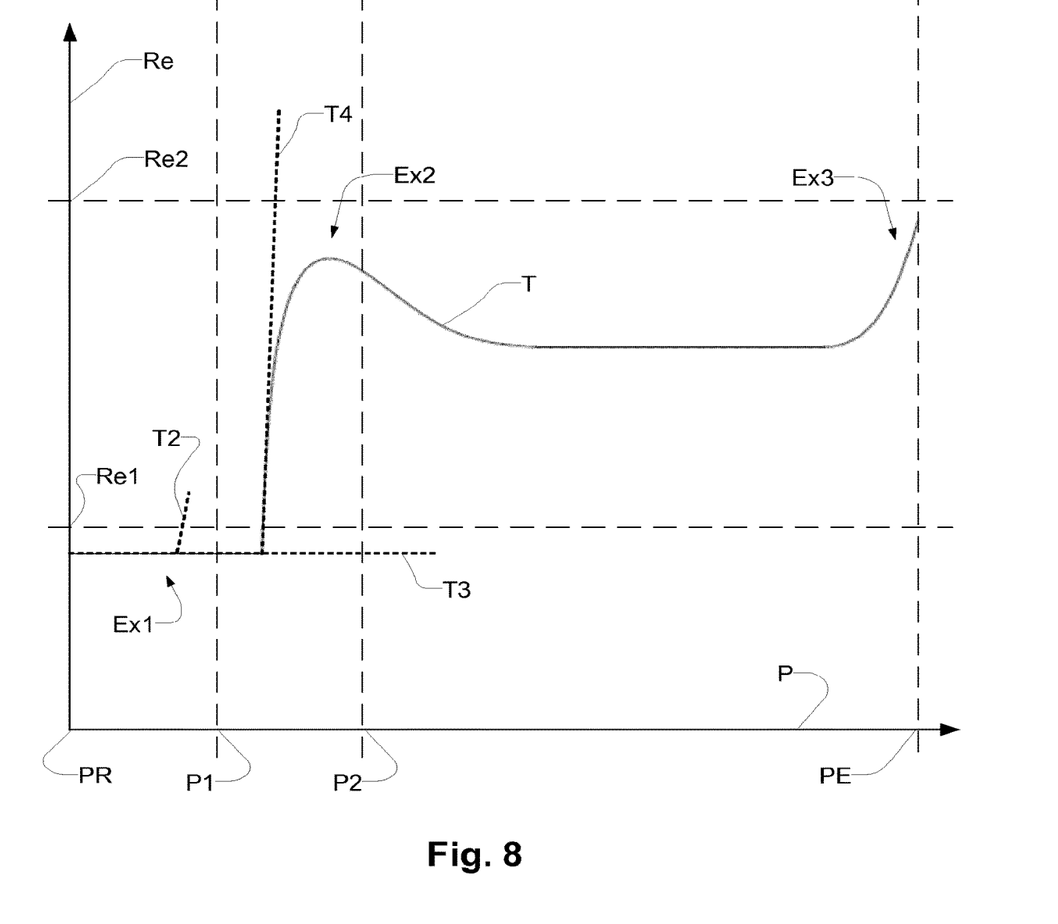
FIG. 8 shows an exemplary graph of resistance vs. position.

FIG. 8 shows an exemplary trace T of resistance Re against movement of the plunger rod dependent on the position P of the plunger rod. The plunger rod is moved from a retracted position PR to an extended position PE. In the beginning of the movement, the resistance against movement of the plunger rod is constant Ex1, e.g. the plunger rod does not yet push a stopper. Afterwards, a plunger rod front end of the plunger rod abuts a first stopper of the cartridge, and the resistance against movement of the plunger rod increases Ex2. The increased resistance is caused by the resistance against movement of the first stopper, e.g. due to frictional force. The resistance may decrease slightly after the first stopper has started moving, as illustrated. When the plunger rod approaches the extended plunger rod position PE, the resistance may increase again Ex3, e.g. due to the first stopper approaching an end of the cartridge.

The trace T is an example of resistance against plunger rod movement when the cartridge received is a new and/or unused and/or normal cartridge. Determining a cartridge parameter may be based on the resistance and/or plunger rod position. Determining the cartridge parameter may be based on one or more thresholds, such as resistance thresholds, such as a low resistance threshold Re1 and/or a high resistance threshold Re2, and/or plunger rod thresholds, such as a first plunger rod threshold P1 and/or a second plunger rod threshold P2.

Other situations, such as situations wherein the cartridge received is apparently used and/or flawed, are exemplified by additional exemplary traces, T2, T3, T4.

Trace T2 illustrates an exemplary situation wherein the resistance against movement increases above the low resistance threshold Re1 before the plunger rod position has reached the first plunger rod threshold P1. Such situation may for example indicate a flawed cartridge, or that something is blocking the plunger rod from moving. Following such situation, the plunger rod may be retracted to the retracted position and an error message may be provided through a user interface.

Trace T3 illustrates an exemplary situation wherein the resistance against movement has not increased above the low resistance threshold Re1 before the plunger rod position has reached the second plunger rod threshold P2. Such situation may for example indicate a cartridge wherein the first stopper is in an advanced position, e.g. a used cartridge. Following such situation, the plunger rod may be retracted to the retracted position and an error message may be provided through a user interface.

Trace T4 illustrates an exemplary situation wherein the resistance against movement increases above a high resistance threshold Re2, e.g. after the plunger rod position has passed the first plunger rod threshold P1. Such situation may for example indicate that the first stopper is blocked from moving, e.g. the cartridge may be flawed. Following such situation, the plunger rod may be retracted to the retracted position and an error message may be provided through a user interface.

The thresholds, such as the low resistance threshold Re1, the high resistance threshold Re2, the first plunger rod threshold P1, and/or the second plunger rod threshold P2 may be individually determined for the cartridge received. For example, a processing unit may be configured to determine one or more of the thresholds, based on a cartridge code feature of the cartridge and/or cartridge assembly received.

Figure 9:
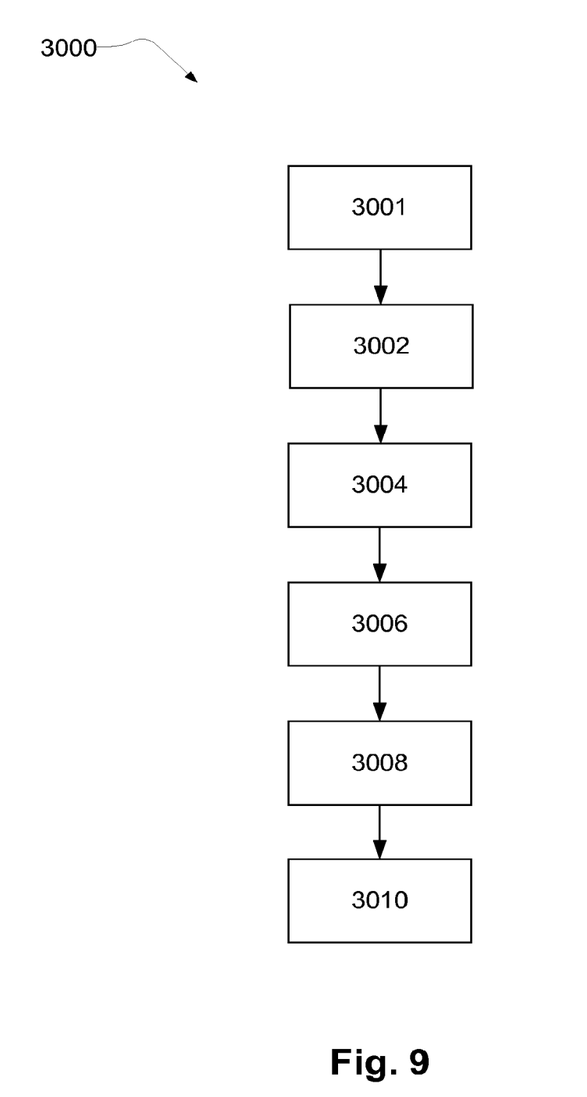
FIG. 9 shows a flow chart of an exemplary method.

FIG. 9 shows a flow chart of an exemplary method 3000 for operating and/or controlling an auto injector, such as the auto injector as described in relation to previous figures.

The method 3000 comprises receiving 3001 a cartridge comprising a first stopper; moving 3002 a plunger rod towards an extended plunger rod position; determining 3004 present plunger rod position; receiving a resistance signal 3006; determining 3008 a cartridge parameter; and adjusting 3010 the movement of the plunger rod.

Receiving 3001 the cartridge may comprise receiving the cartridge in a cartridge receiver of the auto injector.

Moving 3002 the plunger rod may comprise moving the plunger rod from a retracted plunger rod position. Moving 3002 the plunger rod may comprise moving the plunger rod in a first plunger rod direction.

Determining 3004 present plunger rod position may be determined by a processing unit of the auto injector. Determining 3004 present plunger rod position may be based on detection from a sensor, such as an ejection sensor, e.g. comprising a tachometer.

Receiving a resistance signal 3006 may comprise receiving the resistance signal from a resistance sensor. The resistance signal may be indicative of resistance against movement of the plunger rod, such as movement towards the extended plunger rod position, such as movement in the first plunger rod direction.

Determining 3008 a cartridge parameter may comprise determining a cartridge parameter based on the resistance signal and/or the present plunger rod position. For example, the cartridge parameter may be indicative of the cartridge being used if the present plunger rod position has reached a plunger rod threshold and the resistance signal is indicative of resistance against movement of the plunger rod below a low resistance threshold.

Adjusting 3010 the movement of the plunger rod may be based on the cartridge parameter. For example adjusting 3010 the movement may comprise stopping the movement of the plunger rod. Alternatively or additionally, adjusting 3010 the movement may comprise moving the plunger rod to a retracted plunger rod position.

Adjusting 3010 the movement of the plunger rod may comprise adjusting the movement of the plunger rod if the cartridge parameter is indicative of the cartridge being a used cartridge, such as the cartridge parameter being indicative of the present plunger rod position having reached a plunger rod threshold and the resistance signal being indicative of resistance against movement of the plunger rod below a low resistance threshold.

Adjusting 3010 the movement of the plunger rod may comprise adjusting the movement of the plunger rod if the cartridge parameter is indicative of the cartridge being a flawed cartridge, such as the cartridge parameter being indicative of the resistance signal being indicative of resistance against movement of the plunger rod above a high resistance threshold.

Steps of the exemplary method 3000, especially the steps of moving 3002 a plunger rod; determining 3004 present plunger rod position; receiving a resistance signal 3006; determining 3008 a cartridge parameter; and adjusting 3010 the movement of the plunger rod, may be controlled by a processing unit, such as the processing unit of the auto injector.

Exemplary auto injectors, cartridges, systems and methods are set out in the following items:

1. An auto-injector for administering a medicament, comprising:
   a housing;
   a cartridge receiver configured to receive a cartridge comprising a first stopper;
   a drive module coupled to move a plunger rod between a retracted plunger rod position and an extended plunger rod position, the plunger rod being configured to move the first stopper;
   a resistance sensor configured to provide a resistance signal indicative of resistance against movement of the plunger rod; and
   a processing unit coupled to the drive module and to the resistance sensor;
   the processing unit being configured to:
   control the drive module to move the plunger rod towards the extended plunger rod position;
   determine present plunger rod position;
   receive the resistance signal;
   determine a cartridge parameter based on the resistance signal and the present plunger rod position; and
   control the drive module to adjust the movement of the plunger rod based on the cartridge parameter.

2. Auto injector according to item 1, wherein adjusting the movement of the plunger rod comprises stopping the movement of the plunger rod.

3. Auto injector according to any of items 1 or 2, wherein adjusting the movement of the plunger rod comprises moving the plunger rod to the retracted plunger rod position.

4. Auto injector according to any of the preceding items, wherein the processing unit is configured to control the drive module to adjust movement of the plunger rod if the cartridge parameter is indicative of the present plunger rod position having reached a plunger rod threshold and the resistance signal being indicative of resistance against movement of the plunger rod below a low resistance threshold.

5. Auto injector according to any of the preceding items, wherein the processing unit is configured to control the drive module to adjust movement of the plunger rod if the cartridge parameter is indicative of the resistance signal being indicative of resistance against movement of the plunger rod above a high resistance threshold.

6. Auto injector according to item 4 or 5 comprising a code sensor configured to read a cartridge code feature, the processing unit being coupled to the code sensor, the processing unit being configured to receive from the code sensor a code signal indicative of the cartridge code feature and determine the plunger rod threshold and/or the low resistance threshold and/or the high resistance threshold based on the code signal.

7. Auto injector according to any of the preceding items, wherein the resistance sensor is configured to determine electrical power consumed by the drive module.

8. Auto injector according to any of the preceding items, wherein the resistance sensor is configured to measure pressure and/or force applied to a plunger rod front end of the plunger rod.

9. Auto injector according to any of the preceding items comprising a tachometer configured to provide a tachometer signal indicative of a count of revolutions of the drive module, the processing unit being coupled to the tachometer, and the processing unit being configured to receive the tachometer signal and determine the present plunger rod position based on the tachometer signal.

10. Auto injector according to any of the preceding items comprising a user interface coupled to the processing unit, the processing unit being configured to output a user output signal via the user interface based on the cartridge parameter.

11. A system comprising an auto injector according to any of the preceding items, and a cartridge comprising a first stopper, wherein the cartridge is configured to be received in the cartridge receiver.

12. Method for controlling an auto injector, the method comprising:
   receiving a cartridge comprising a first stopper;
   moving a plunger rod towards an extended plunger rod position;
   determining present plunger rod position;
   receiving a resistance signal indicative of resistance against movement of the plunger rod;
   determining a cartridge parameter based on the resistance signal and the present plunger rod position; and
   adjusting the movement of the plunger rod based on the cartridge parameter.

13. Method according to item 12, wherein adjusting the movement of the plunger rod comprises stopping the movement of the plunger rod.

14. Method according to any of items 12 or 13, wherein adjusting the movement of the plunger rod comprises moving the plunger rod to a retracted plunger rod position.

15. Method according to any of items 12-14, wherein adjusting the movement of the plunger rod comprises adjusting the movement of the plunger rod if the cartridge parameter is indicative of the present plunger rod position having reached a plunger rod threshold and the resistance signal being indicative of resistance against movement of the plunger rod below a low resistance threshold.

16. Method according to any of items 12-15, wherein adjusting the movement of the plunger rod comprises adjusting the movement of the plunger rod if the cartridge parameter is indicative of the resistance signal being indicative of resistance against movement of the plunger rod above a high resistance threshold.

17. Method according to any of claims 12-16 comprising receiving a code signal indicative of a cartridge code feature and determining the plunger rod threshold and/or the low resistance threshold and/or the high resistance threshold based on the code signal.

The invention claimed is:

1. An auto-injector for administering a medicament, comprising:
   a housing;
   a cartridge receiver configured to receive a cartridge comprising a first stopper;
   a drive module coupled to move a plunger rod between a retracted plunger rod position and an extended plunger rod position, the plunger rod being configured to move the first stopper;
   a resistance sensor configured to provide a resistance signal indicative of resistance against movement of the plunger rod; and
   a processing unit coupled to the drive module and to the resistance sensor;

wherein the processing unit is configured to:
control the drive module to move the plunger rod towards the extended plunger rod position;
determine present plunger rod position;
receive the resistance signal;
determine a cartridge parameter based on the resistance signal and the present plunger rod position; and
control the drive module to adjust the movement of the plunger rod based on the cartridge parameter, and
wherein the processing unit is configured to control the drive module to adjust movement of the plunger rod if the cartridge parameter is indicative of the present plunger rod position having reached a plunger rod threshold and the resistance signal being indicative of resistance against movement of the plunger rod below a low resistance threshold.

2. The auto injector according to claim 1, wherein the processing unit is further configured to control the drive module to adjust movement of the plunger rod if the cartridge parameter is indicative of the resistance signal being indicative of resistance against movement of the plunger rod above a high resistance threshold.

3. The auto injector according to claim 2, comprising a code sensor configured to read a cartridge code feature, the processing unit being coupled to the code sensor, the processing unit being configured to receive from the code sensor a code signal indicative of the cartridge code feature and determine the high resistance threshold based on the code signal.

4. The auto injector according to claim 1, wherein adjusting the movement of the plunger rod comprises stopping the movement of the plunger rod.

5. The auto injector according to claim 1, wherein adjusting the movement of the plunger rod comprises moving the plunger rod to the retracted plunger rod position.

6. The auto injector according to claim 1, comprising a code sensor configured to read a cartridge code feature, the processing unit being coupled to the code sensor, the processing unit being configured to receive from the code sensor a code signal indicative of the cartridge code feature and determine the plunger rod threshold or the low resistance threshold based on the code signal.

7. The auto injector according to claim 1, wherein the resistance sensor is configured to determine electrical power consumed by the drive module.

8. The auto injector according to claim 1, wherein the resistance sensor is configured to measure pressure or force applied to a plunger rod front end of the plunger rod.

9. The auto injector according to claim 1, comprising a tachometer configured to provide a tachometer signal indicative of a count of revolutions of the drive module, the processing unit being coupled to the tachometer, and the processing unit being configured to receive the tachometer signal and determine the present plunger rod position based on the tachometer signal.

10. The auto injector according to claim 1, comprising a user interface coupled to the processing unit, the processing unit being configured to output a user output signal via the user interface based on the cartridge parameter.

11. A system comprising an auto injector according to claim 1, and a cartridge comprising a first stopper, wherein the cartridge is configured to be received in the cartridge receiver.

12. A method for controlling an auto injector, the method comprising:
receiving a cartridge comprising a first stopper;
moving a plunger rod towards an extended plunger rod position;
determining present plunger rod position;
receiving a resistance signal indicative of resistance against movement of the plunger rod;
determining a cartridge parameter based on the resistance signal and the present plunger rod position; and
adjusting the movement of the plunger rod based on the cartridge parameter if the cartridge parameter is indicative of the present plunger rod position having reached a plunger rod threshold and the resistance signal being indicative of resistance against movement of the plunger rod below a low resistance threshold.

13. The method according to claim 12, further comprising adjusting the movement of the plunger rod based on the cartridge parameter if the cartridge parameter is indicative of the resistance signal being indicative of resistance against movement of the plunger rod above a high resistance threshold.

14. The method according to claim 12, wherein adjusting the movement of the plunger rod comprises stopping the movement of the plunger rod.

15. The method according to claim 12, wherein adjusting the movement of the plunger rod comprises moving the plunger rod to a retracted plunger rod position.

16. The method according to claim 12, comprising receiving a code signal indicative of a cartridge code feature and determining the plunger rod threshold or the low resistance threshold or the high resistance threshold based on the code signal.

* * * * *